United States Patent [19]

Ohsaka et al.

[11] 4,288,376

[45] Sep. 8, 1981

[54] PROCESS FOR PREPARING HEXAFLUOROPROPENE OXIDE

[75] Inventors: Yohnosuke Ohsaka, Takatsuki; Takashi Tohzuka, Settsu, both of Japan

[73] Assignee: Daikin Kogyo Co., Ltd., Osaka, Japan

[21] Appl. No.: 170,153

[22] Filed: Jul. 18, 1980

[30] Foreign Application Priority Data

Jul. 18, 1979 [JP] Japan .................................. 54/91827

[51] Int. Cl.$^3$ .......................................... C07D 301/08
[52] U.S. Cl. ............................................... 260/348.23
[58] Field of Search .................................... 260/348.23

[56] References Cited

U.S. PATENT DOCUMENTS

| | | | |
|---|---|---|---|
| 3,536,733 | 10/1970 | Carlson | 260/348.23 |
| 3,775,438 | 11/1973 | Cavanaugh | 260/348.23 |
| 3,775,439 | 11/1973 | Atkins | 260/348.23 |

FOREIGN PATENT DOCUMENTS 52-53804  4/1977  Japan .
52-53805  4/1977  Japan .
52-53806  4/1977  Japan .

*Primary Examiner*—Norma S. Milestone
*Attorney, Agent, or Firm*—Birch, Stewart, Kolasch & Birch

[57] ABSTRACT

Hexafluoropropene oxide is prepared with good conversion and high selectivity by reacting hexafluoropropene with oxygen in the presence of at least one barium compound selected from the group consisting of barium oxide, barium hydroxide and barium salts as a catalyst.

3 Claims, No Drawings

PROCESS FOR PREPARING HEXAFLUOROPROPENE OXIDE

BACKGROUND OF THE INVENTION

This invention relates to a process for preparing hexafluoropropene oxide. More particularly, it relates to a process for preparing hexafluoropropene oxide by reacting hexafluoropropene with oxygen.

Hexafluoropropene oxide is useful as an intermediate of various valuable fluorine-containing compounds such as perfluorovinyl ether, of which a low molecular weight polymer is used as a heat resistance fluid.

For preparation of hexafluoropropene oxide, there is known a process comprising reacting hexafluoropropene with oxygen in a liquid medium or in a gaseous phase. The reaction in a gaseous phase is particularly favorable for industrial production of hexafluoropropene oxide, because of its operational advantage and other ones.

In the gaseous phase reaction, the reaction preferably proceeds in the presence of a catalyst. As such catalyst, there are known several ones including silica gel treated with hydrogen chloride and then with oxygen and hexafluoropropene and/or hexafluoropropene oxide (U.S. Pat. No. 3,775,439), a catalyst mainly composed of copper supported on silica alumina (Japanese Patent Publication (unexamined) No. 53804/1977), a zeolite catalyst ion-exchanged with a transition metal (Japanese Patent Publication (unexamined) No. 53805/1977) and a catalyst mainly composed of copper supported on silica gel (Japanese Patent Publication (unexamined) No. 53806/1977). The preparation of these catalysts is, however, very troublesome.

SUMMARY OF THE INVENTION

As the result of an extensive study, it has now been found that a barium compound, which is readily available at a low cost, is an effective catalyst for the reaction of hexafluoropropene with oxygen and affords hexafluoropropene oxide in such reaction with good conversion and high selectivity.

According to the present invention, there is provided a process for preparing hexafluoropropene oxide which comprises reacting hexafluoropropene with oxygen in the presence of a barium compound selected from the group consisting of barium oxide, barium hydroxide and barium salts as a catalyst.

The barium compound to be used as the catalyst in this invention may be a reagent grade. Before a use, it is preferably heated under the stream of an inert gas (e.g. nitrogen) at a temperature not lower than the reaction temperature to be adopted for the reaction of hexafluoropropene with oxygen. If any gaseous material is released during such heat treatment, its thorough release is favorable. For instance, in the case of barium carbonate, the release of carbon dioxide is to be completed.

The barium salt may be an organic one or an inorganic one, but an inorganic one is usually preferred because, it evolves a little or no gaseous material at the reaction temperature. Examples of the inorganic salt are barium fluoride, barium chloride, barium sulfate, barium carbonate, barium nitrate, etc.

Hexafluoropropene and oxygen may be used usually in a molar proportion of from 0.1:1 to 10:1, preferably of from 0.5:1 to 5:1. Oxygen is favorable in a pure form but can be in a diluted form. For dilution an inert gas such as nitrogen, helium or carbon dioxide may be used. Air is also used.

The reaction can be carried out batchwise or continuously. In the continuous process, the reaction is effected by passing a gaseous mixture of hexafluoropropene and oxygen through a fixed or fluidized bed containing the barium compound.

The preferred range of temperature is from 100° to 350° C., particularly from 150° to 300° C. At a temperature lower than 100° C., the conversion of hexafluoropropene is lower. At a temperature higher than 350° C., the selectivity to hexafluoropropene oxide is lower. An extremely high temperature is particularly undesirable because it produces a large amount of decomposition products. Pressure is not particularly limited. Usually a pressure of 0.5 to 20 atm., preferably of 1 to 5 atm. is employed. The contact time depends on the other reaction conditions, particularly on the reaction temperature. Similar to other ordinary reactions, the contact time should be shorter at a higher temperature and longer at a lower temperature. Usually it is from 10 to 300 seconds, preferably from 30 to 200 seconds.

From the reaction mixture, hexafluoropropene oxide can be isolated by a conventional method, for example, extraction and/or distillation.

PREFERRED EMBODIMENTS

The present invention will be hereinafter explained in detail by the following Examples.

EXAMPLE 1

Barium oxide was ground, and the powder (7.8 g) of 20 to 60 mesh was charged into a glass made for reactor of 3 mm in inner diameter and 0.5 m in length. The reactor was heated under nitrogen stream at 500° C. for 4 hours and then cooled to 250° C. At the same temperature, a gaseous mixture of hexafluoropropene and oxygen in a molar ratio of 2:1 was passed through the reactor with a space velocity of 100 $hr^{-1}$.

The composition of the exit gas, the conversion of hexafluoropropene and the selectivity to hexafluoropropene oxide are shown in Table 1.

EXAMPLE 2

In the same manner as in Example 1 but using barium sulfate (5.6 g) of 20 to 60 mesh in place of barium oxide, the reaction was carried out. The results are shown in Table 1.

EXAMPLE 3

Barium carbonate was shaped into pellets, having a diameter of 5 mm and a length of 3 mm, and heated at 900° C. for 5 hours in an electric furnace. The thus prepared pellets (40 g) were charged into a Hastelloy C made reactor of $\frac{3}{4}$ inch in diameter and 1 m in length. Then, the reactor was heated under nitrogen stream at 400° C. for 3 hours and cooled to 200° C. At the same temperature, a gaseous mixture of hexafluoropropene and oxygen in a molar ratio of 2:1 was passed through the reactor with a space velocity of 60 $hr^{-1}$. The results are shown in Table 1.

EXAMPLE 4

Equimolar amounts of barium oxide and barium fluoride were mixed, and the mixture was added to deionized water, heated, stirred to emulsify them enough and then dried at 100° C. for 24 hours. After cooling, the residue was ground and heated at 600° C. for 5 hours in an electric furnace. Of the obtained powder, a part of 20 to 60 mesh (7.8 g) was charged into a glass made reactor of 3 mm in inner diameter and 0.5 m in length. The reactor was heated under nitrogen stream at 400° C. for 3 hours and cooled to 220° C. At the same temperature, a gaseous mixture of hexafluoropropene and oxygen in a molar ratio of 2:1 was passed through the reactor with a space velocity of 80 hr$^{-1}$. The results are shown in Table 1.

TABLE 1

| Example No. | Exit gas composition (% by mole) | | | | | | Conversion (%) | Selectivity[1] (%) |
| --- | --- | --- | --- | --- | --- | --- | --- | --- |
| | $CO_2$ | $COF_2$ | $CF_3COF$ | $CF_3CF\underset{O}{\overset{\diagdown\ \diagup}{\text{———}}}CF_2$ | $CF_3CF{=}CF_2$ | High boiling point compounds | | |
| 1 | 6.0 | 12.1 | 0.6 | 14.3 | 66.5 | 0.5 | 24.2 | 67.4 |
| 2 | 6.5 | 9.7 | 5.3 | 15.1 | 62.4 | 1.0 | 28.6 | 60.3 |
| 3 | 5.3 | 8.4 | 4.6 | 15.0 | 66.0 | 0.7 | 26.1 | 64.3 |
| 4 | 8.1 | 16.3 | 0.2 | 20.2 | 55.1 | 0.1 | 34.1 | 70.7 |

[1] selectivity = $\dfrac{\text{amount of formed hexafluoropropene oxide}}{\text{amount of conversed hexafluoropropene}} \times 100$ The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing hexafluoropropene oxide which comprises reacting hexafluoropropene with oxygen in the presence of at least one barium compound selected from the group consisting of barium oxide, barium hydroxide and inorganic barium salt as a catalyst at a temperature of from 100° to 350° C.

2. The process according to claim 1, wherein the molar ratio of hexafluoropropene and oxygen is from 0.1:1 to 10:1.

3. The process according to claim 1, wherein said barium compound is an inorganic barium salt selected from at least one member of the group consisting of barium fluoride, barium chloride, barium sulfate, barium carbonate, and barium nitrate.

* * * * *